United States Patent [19]

Pexa

[11] Patent Number: 4,596,557
[45] Date of Patent: Jun. 24, 1986

[54] AIR ELIMINATOR FOR INTRAVENOUS TUBE

[76] Inventor: Charles E. Pexa, 1200 Lyman Ave., Wayzata, Minn. 55391

[21] Appl. No.: 624,777

[22] Filed: Jun. 26, 1984

[51] Int. Cl.⁴ ............................................. A61M 37/00
[52] U.S. Cl. ..................................... 604/86; 604/284
[58] Field of Search .............. 604/284, 256, 257, 205, 604/93, 83, 86

[56] References Cited

U.S. PATENT DOCUMENTS

| | | | |
|---|---|---|---|
| 3,994,293 | 11/1976 | Ferro | 604/83 |
| 4,013,064 | 3/1977 | Patel et al. | 604/86 |
| 4,121,585 | 10/1978 | Becker, Jr. | 604/86 |
| 4,289,129 | 9/1981 | Turner | 604/86 |

*Primary Examiner*—John D. Yasko
*Attorney, Agent, or Firm*—Hugh D. Jaeger

[57] ABSTRACT

Solid, soft, penetrable, non-coring material for filling a side-arm injection port of an intravenous tube. The material occludes the injection port or other site where air or administered medications may be trapped in the tubing. The material fills the area that lies out of the main stream of the intravenous infusate while allowing medication injection through the non-coring material. The material also decreases or practically eliminates any weeping from the numerous injections into a port, lessening the chance for sepsis.

4 Claims, 2 Drawing Figures

AIR ELIMINATOR FOR INTRAVENOUS TUBE

BACKGROUND OF THE INVENTION

1. Field of the Invention

The present invention pertains to an intravenous infusion line, and more particularly, pertains to an intravenous infusion line including a non-coring material at a side-arm injection port. This eliminates any air or medication trappings.

2. Description of the Prior Art

Traditionally, air pockets have been created in intravenous infusion lines at the side-arm injection ports because the injection ports are outside of the main flushing stream when the intravenous is first run. The air must be removed and has been done so by needle aspiration or by striking the port to jar air bubbles loose. These air bubbles must again be cleared from the remainder of the line.

Hazards of air embolism are death, cerebral vascular accidents, such as a stroke, pulmonary hypertension or the like. Ventricular septal defects allow air to shunt across the heart and go into the arterial circulation with potential serious consequences. Medication can, therefore, accumulate in these areas denying the patient of needed medication or allowing for uncontrolled dispersal.

The prior art is replete with references identifying this problem, but as of this time, the problem has not been solved.

The present invention overcomes the disadvantages of the prior art by providing a solid, soft, penetrable, non-coring material which fills the side-arm injection ports of intravenous tubing.

SUMMARY OF THE INVENTION

The general purpose of the present invention is to provide a solid, soft, penetrable, non-coring material for filling the side-arm injection ports of an intravenous tubing. The material fills the area that lies out of the main stream of the intravenous infusate, while allowing medical injection.

According to one embodiment of the present invention, there is provided an intravenous tube including a side-arm injection port, and a solid, soft, penetrable, non-coring material filling the side-arm injection port including a plug having an angular bottom for substantially coinciding with the intravenous fluid flow.

One of the significant aspects and features of the present invention is an air eliminator for an intravenous tube which provides a least amount, if any, or minimal air trappings due to a soft, solid, penetrable, non-coring material filling the dead space in the current system. Also, the same material provides for a least, or no drug accumulation.

Another significant aspect and feature of the present invention of an air eliminator for intravenous tubing is a solid, soft, penetrable, non-coring material which fills a side-arm injection port which provides for minimal or practically no infusate leaking after multiple injections and thus decreasing any chances of infection, as currently occurs.

Having best described the principal embodiment of the present invention, it is an object hereof to provide an air eliminator of a soft, solid, penetrable, non-coring material for a side-arm injection port of an intravenous tube.

One object of the present invention is a soft, solid, penetrable, non-coring material which fills sidearm injection ports and occludes the injection ports or other site where air or administered medications may be trapped in the tubing. The added bulk decreases any weeping from numerous injections into a port.

DESCRIPTION OF THE PREFERRED EMBODIMENTS

Figure 1:
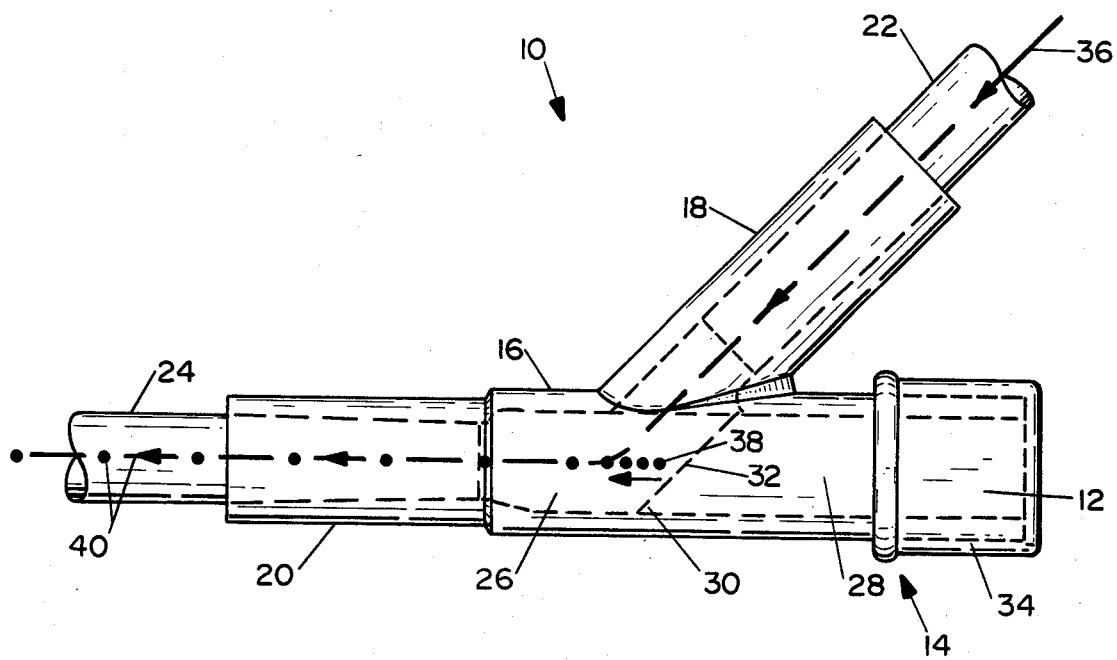
FIG. 1 illustrates a side view of an intravenous tube with a side-arm injection port and an air eliminator; and, FIG. 2 illustrates a cross section of FIG. 1.

FIG. 1 illustrates a side view of a air eliminator 10, the present invention, in a side-arm injection port 12 of an intravenous tube 14. The intravenous tube 14 includes a main body 16, a main stream input port 18, the side-arm injection port 12 connected thereto, and a main stream output port 20. The input intravenous tubing 22 and the output intravenous tubing 24 connect between the main body 16. The chamber area 26 provides for mixing the intravenous solution 36 and the injected medication 38. The air eliminator 10 contains a solid, soft, penetrable, non-coring, soft rubber material 28 for a cylindrical member including an angled end 30 and a flat other end 32. A rubber cap 34 surrounds the side-arm injection port 12. The rubber cap 34 and eliminator material 28 are one piece as illustrated, but can be formed as two pieces as so desired.

The main stream intravenous fluid 36 flows through the input intravenous tubing 22 and mixes with the injected fluid 38 providing for a main stream injected fluid mix 40. The angled flat end 32 geometrically conforms to intravenous mainline flow and decreases turbulence.

Figure 2:
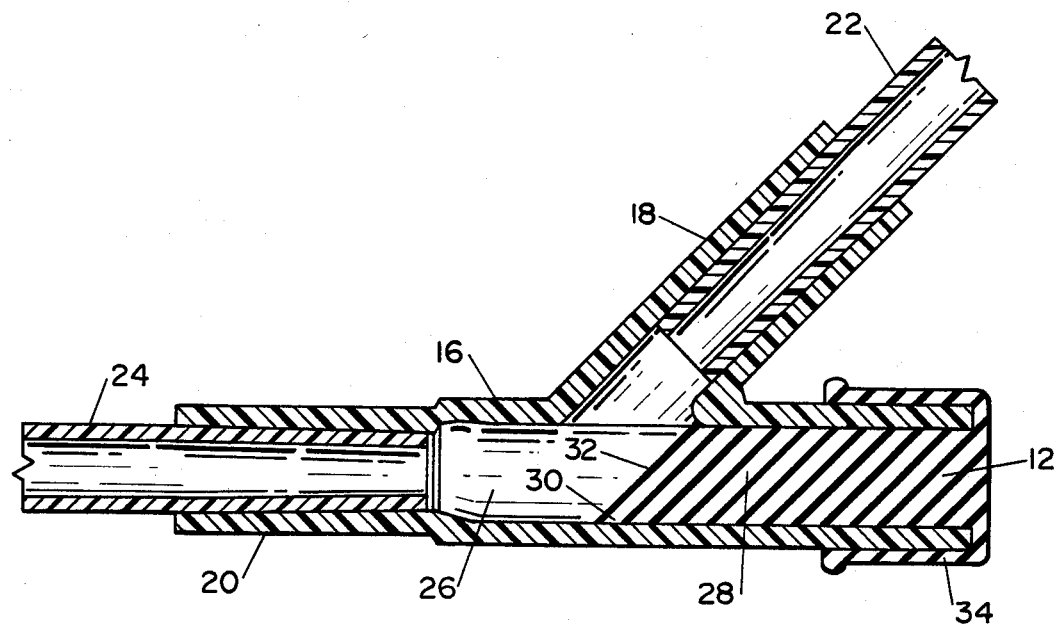

FIG. 2 illustrates a sectional view where all numerals correspond to those elements previously described. Particularly illustrated in the air eliminator 10 is the soft, solid, non-coring material 28.

I claim:

1. In combination, intravenous tube with side-arm injection port and air eliminator comprising:
   a. intravenous tube means with a side-arm port means; and,
   b. air eliminator means located in the side-arm port means and including an angled flat end and an end that conforms to intravenous mainline flow and decreases turbulence.

2. Combination of claim 1 wherein said air eliminator means is made of solid, soft, penetrable, non-coring, rubber material.

3. Combination of claim 1 wherein said air eliminator means comprises a cylindrical member including an angled end and a cap end.

4. Combination of claim 3 wherein said cap end engages over a side port of an intravenous tube.

* * * * *